(12) United States Patent
Mobasser et al.

(10) Patent No.: US 9,949,776 B2
(45) Date of Patent: Apr. 24, 2018

(54) AWL-TIPPED PEDICLE SCREW AND METHOD OF IMPLANTING SAME

(71) Applicant: WARSAW ORTHOPEDIC, INC., Warsaw, IN (US)

(72) Inventors: Jean-Pierre Mobasser, Indianapolis, IN (US); Y. Raja Rampersaud, Toronto (CA)

(73) Assignee: Warsaw Orhtopedic, Inc., Warsaw, IN (US)

( * ) Notice: Subject to any disclaimer, the term of this patent is extended or adjusted under 35 U.S.C. 154(b) by 0 days.

(21) Appl. No.: 15/159,426

(22) Filed: May 19, 2016

(65) Prior Publication Data

US 2016/0256209 A1    Sep. 8, 2016

Related U.S. Application Data

(63) Continuation of application No. 14/011,052, filed on Aug. 27, 2013, now abandoned, which is a continuation-in-part of application No. 13/117,669, filed on May 27, 2011, now abandoned.

(60) Provisional application No. 61/396,564, filed on May 28, 2010.

(51) Int. Cl.
  *A61B 17/86* (2006.01)
  *A61B 17/70* (2006.01)
(52) U.S. Cl.
  CPC ........ *A61B 17/8635* (2013.01); *A61B 17/863* (2013.01); *A61B 17/7037* (2013.01)
(58) Field of Classification Search
  CPC ... A61B 17/86; A61B 17/8605; A61B 17/861; A61B 17/8615; A61B 17/862; A61B 17/8625; A61B 17/863; A61B 17/8635; A61B 17/866; F16B 25/0015
  USPC ....... 606/300–321, 246–279; 411/386, 387.1
  See application file for complete search history.

(56) References Cited

U.S. PATENT DOCUMENTS

| | | | | | |
|---|---|---|---|---|---|
| 373,074 | A | * | 11/1887 | Jones | F16B 25/00 411/386 |
| 2,871,752 | A | * | 2/1959 | Stern | F16B 25/0031 411/387.1 |
| 4,068,554 | A | * | 1/1978 | Hirabayashi | F16B 25/0021 411/386 |
| 4,311,423 | A | * | 1/1982 | Hirabayashi | F16B 25/0021 411/387.4 |
| 4,572,720 | A | * | 2/1986 | Rockenfeller | F16B 15/06 411/311 |

(Continued)

OTHER PUBLICATIONS

Yan Chen, Hong-In Shin, Hee-Moon Kyung Biomechanical and histological comparison of self-drilling and self-tapping orthodontic microimplants in dogs American Journal of Orthodontics and Dentofacial Orthopedics, vol. 133, Issue 1, Jan. 2008, pp. 44-50.

(Continued)

*Primary Examiner* — Eric S Gibson

(57) ABSTRACT

A bone screw and method of inserting the same is disclosed. In one example, the bone screw includes an awl tip for creating a pilot hole in the pedicle of a vertebra without having to predrill a starter hole. One or more threads located adjacent to the awl tip engage the wall of the pilot hole and draw the screw into the bone, thereby eliminating the need to drill and tap a hole in the bone prior to implantation of the screw.

20 Claims, 9 Drawing Sheets

(56) References Cited

U.S. PATENT DOCUMENTS

| | | | | |
|---|---|---|---|---|
| 4,978,350 A * | 12/1990 | Wagenknecht | A61B 17/8635 | 411/387.7 |
| 5,098,435 A * | 3/1992 | Stednitz | A61B 17/1637 | 411/387.5 |
| 5,199,839 A * | 4/1993 | DeHaitre | F16B 23/0076 | 411/387.3 |
| 5,334,204 A * | 8/1994 | Clewett | A61B 17/8625 | 606/312 |
| 5,492,442 A * | 2/1996 | Lasner | F16B 33/02 | 411/308 |
| 5,522,817 A * | 6/1996 | Sander | A61B 17/0642 | 606/329 |
| 5,759,003 A * | 6/1998 | Greenway | F16B 25/0015 | 411/399 |
| 5,792,142 A * | 8/1998 | Galitzer | A61B 17/8635 | 411/302 |
| 5,797,914 A * | 8/1998 | Leibinger | A61B 17/8635 | 411/387.8 |
| 5,925,048 A * | 7/1999 | Ahmad | A61B 17/8605 | 606/308 |
| 6,210,376 B1 * | 4/2001 | Grayson | A61B 17/3472 | 604/264 |
| 6,248,108 B1 * | 6/2001 | Tormala | A61B 17/8625 | 411/533 |
| 6,398,785 B2 * | 6/2002 | Carchidi | A61B 17/8615 | 606/312 |
| 6,440,136 B1 * | 8/2002 | Gambale | A61B 17/8605 | 411/402 |
| 6,565,573 B1 * | 5/2003 | Ferrante | A61B 17/8888 | 606/308 |
| 7,001,389 B1 * | 2/2006 | Navarro | A61B 17/8047 | 606/281 |
| 7,819,905 B2 * | 10/2010 | Newcomb | A61B 17/8625 | 606/311 |
| 7,955,364 B2 * | 6/2011 | Ziolo | A61B 17/8057 | 606/291 |
| 8,192,124 B2 * | 6/2012 | Wolpert | F16B 25/0015 | 411/386 |
| 8,414,628 B2 * | 4/2013 | Melkent | A61B 17/7001 | 606/264 |
| 8,668,725 B2 * | 3/2014 | Smisson, III | A61B 17/863 | 606/286 |
| 8,998,968 B1 * | 4/2015 | Brow | A61B 17/8695 | 606/306 |
| 9,079,263 B2 * | 7/2015 | Reed | B23G 1/02 | |
| 2001/0004694 A1 * | 6/2001 | Carchidi | A61B 17/8615 | 606/312 |
| 2002/0044844 A1 * | 4/2002 | Andronica | B23B 51/00 | 408/199 |
| 2004/0044345 A1 * | 3/2004 | DeMoss | A61B 17/8625 | 606/916 |
| 2004/0068261 A1 * | 4/2004 | Fourcault | A61B 17/863 | 606/67 |
| 2004/0138662 A1 * | 7/2004 | Landry | A61B 17/1604 | 606/86 A |
| 2006/0079903 A1 * | 4/2006 | Wong | A61B 17/1735 | 606/916 |
| 2006/0149263 A1 * | 7/2006 | Newcomb | A61B 17/8625 | 606/311 |
| 2006/0183079 A1 * | 8/2006 | Galvan | A61B 17/8605 | 433/174 |
| 2007/0083206 A1 * | 4/2007 | Du | A61B 17/8635 | 606/279 |
| 2008/0077139 A1 * | 3/2008 | Landry | A61B 17/1757 | 606/86 A |
| 2008/0097443 A1 * | 4/2008 | Campbell | A61B 17/7059 | 606/281 |
| 2008/0177335 A1 * | 7/2008 | Melkent | A61B 17/7001 | 606/309 |
| 2009/0018589 A1 * | 1/2009 | Smisson, III | A61B 17/863 | 606/301 |
| 2009/0036933 A1 * | 2/2009 | Dube | A61B 17/1671 | 606/282 |
| 2009/0142159 A1 * | 6/2009 | Wolpert | F16B 25/0015 | 411/387.1 |
| 2009/0187194 A1 * | 7/2009 | Hamada | A61B 17/7001 | 606/104 |
| 2009/0198291 A1 * | 8/2009 | Kevin | A61B 17/863 | 606/305 |
| 2009/0326545 A1 * | 12/2009 | Schaffhausen | A61B 17/8891 | 606/104 |
| 2010/0004693 A1 * | 1/2010 | Miller | A61B 17/7001 | 606/308 |
| 2010/0145341 A1 * | 6/2010 | Ranck | A61B 17/1615 | 606/80 |
| 2010/0211118 A1 * | 8/2010 | Christen | A61B 17/8635 | 606/312 |
| 2010/0280558 A1 * | 11/2010 | Biyani | A61B 17/8685 | 606/318 |
| 2011/0081626 A1 * | 4/2011 | Hurson | A61C 8/0022 | 433/174 |
| 2011/0085866 A1 * | 4/2011 | Evatt | B27G 15/00 | 408/213 |
| 2011/0106157 A1 * | 5/2011 | Melkent | A61B 17/863 | 606/246 |
| 2011/0295319 A1 * | 12/2011 | Duplessis | A61B 17/1655 | 606/264 |
| 2012/0136398 A1 * | 5/2012 | Mobasser | A61B 17/8635 | 606/311 |
| 2012/0232599 A1 * | 9/2012 | Schoenly | A61B 17/8635 | 606/315 |
| 2013/0158610 A1 * | 6/2013 | Hernandez | A61F 2/4081 | 606/315 |
| 2013/0231708 A1 * | 9/2013 | Melkent | A61B 17/7001 | 606/308 |
| 2014/0005728 A1 * | 1/2014 | Koay | A61B 17/8057 | 606/281 |
| 2014/0053696 A1 * | 2/2014 | Reed | B23G 1/02 | 82/1.11 |
| 2014/0058461 A1 * | 2/2014 | Black | A61B 17/864 | 606/314 |
| 2014/0243912 A1 * | 8/2014 | Mobasser | A61B 17/8635 | 606/311 |
| 2014/0277188 A1 * | 9/2014 | Poulos | A61B 17/1655 | 606/304 |
| 2015/0196336 A1 * | 7/2015 | Whipple | A61B 17/863 | 606/312 |

OTHER PUBLICATIONS

Emily Hung DDS, MS1; Donald Oliver DDS, MS2; Ki Beom Kim DDS, PhD2; Hee-Moon Kyung DDS, PhD3; Peter H. Buschang PhD4 Effects of Pilot Hole Size and Bone Density on Miniscrew Implants' Stability Clinical Implant Dentistry and Related Research, vol. 13, Issue 1, Mar. 2011.

Heidemann W, Gerlach K L, Department of Maxillofacial Surgery, Otto-Von-Guericke University Magdeburg, Leipziger Strasse 44 39120 Magdeburg Germany Clinical applications of drill free screws in maxillofacial surgery Journal of cranio-maxillo-facial surgery, 1999, vol. 27, No. 4, pp. 252-255.

Goezler, Juliana Gonçalves; Avelar, Rafael Linard; De Oliveira, Rogério Belle PhD†, Hubler, Roberto PhD‡; Silveira, Roger Lanes; Machado, Rosilene Andrea Self-Drilling and Self-Tapping Screws, an Ultrastructural Study Journal of Craniofacial Surgery, Mar. 2010, vol. 21, Issue 2, pp. 513-515.

Geerling J (Reprint); Gosling T; Gosling A; Ortega G; Kendoff D; Citak M; Krettek C; Hufner T (E-Mail: Jens.Geerling@Planet-Interkom.de); Hannover Med SCH; Trauma Dept, Carl Neuberg STR 1, D-30625 Hannover, Germany (Reprint); Hannover Med SCH, Trauma Dept, D-30625 Hannover, Germany; Scottsdale Healthcare, Sonoran Orthopaed Trauma Surg, Scottsdale, AZ.

* cited by examiner

AWL-TIPPED PEDICLE SCREW AND METHOD OF IMPLANTING SAME

CROSS REFERENCE TO RELATED APPLICATIONS

This application is a continuation of and claims priority to co-pending U.S. patent application Ser. No. 14/011,052, which is a continuation-in-part of and claims priority to U.S. patent application Ser. No. 13/117,669 filed on May 27, 2011, which claims priority to U.S. Provisional Patent No. 61/396,564 filed on May 28, 2010. These applications are incorporated herein by reference, in their entireties.

TECHNICAL FIELD

The claimed technology relates generally to medical devices and more particularly to bone screws and methods of implanting the same.

BACKGROUND

A variety of threaded fasteners have been developed for use in orthopedic surgical procedures to secure bone fragments, reattach ligaments or soft tissue to bones, or to hold bones in relative position to one another. One variety of bone screws used in the vertebrae of the spine are called pedicle screws, so named because they are inserted into the pedicle of the vertebral body. Pedicle screws are commonly used along with rods and screws to immobilize a portion of the spinal column. In other applications, pedicle screws are inserted into a series of vertebrae and one or more metal rods are secured to the heads of the screws, typically using set screws or some other securing means.

Current pedicle screw designs require multiple steps to insure proper implantation into the vertebral body. Typically, an entry point is made into the pedicle using a high speed drill bit or an awl to create a pilot hole. In some instances, the pilot hole is enlarged using larger diameter drill bits. The pilot hole may then be probed with an instrument to detect any breaches in the pedicle wall. After the integrity of the pilot hole wall is confirmed, the pilot is then tapped to create a track in the hole wall for the screw to follow using a tap. Finally, the screw may be implanted into the prepared hole.

Every surgical procedure carries with it a risk of complications. Procedures which require multiple steps such as pedicle screw implantation create the potential for the patient to experience complications with each step. Additionally, the chances for a surgeon to make a mistake due to fatigue during long procedures involving multiple screws increases with the number of steps required for placement of each screw. Thus there is a need for an improved bone screw which reduces the number of steps required for implantation of the screw into bone.

SUMMARY

In one embodiment, a bone screw is provided that comprises a tip portion comprising an awl tip. The awl tip has a pyramidal configuration capable of creating a hole in bone. The bone screw includes a shank portion proximate to said tip portion, a head portion proximate to said shank portion and at least one helical thread which begins at said tip portion and continues through said shank portion. In some embodiments, said awl tip comprises three flat surfaces that define said pyramidal configuration. In some embodiments, said flat surfaces intersecting at a common point

BRIEF DESCRIPTION OF THE DRAWINGS

The present disclosure will become more readily apparent from the specific description accompanied by the following drawings, in which.

DETAILED DESCRIPTION

Figure 1:
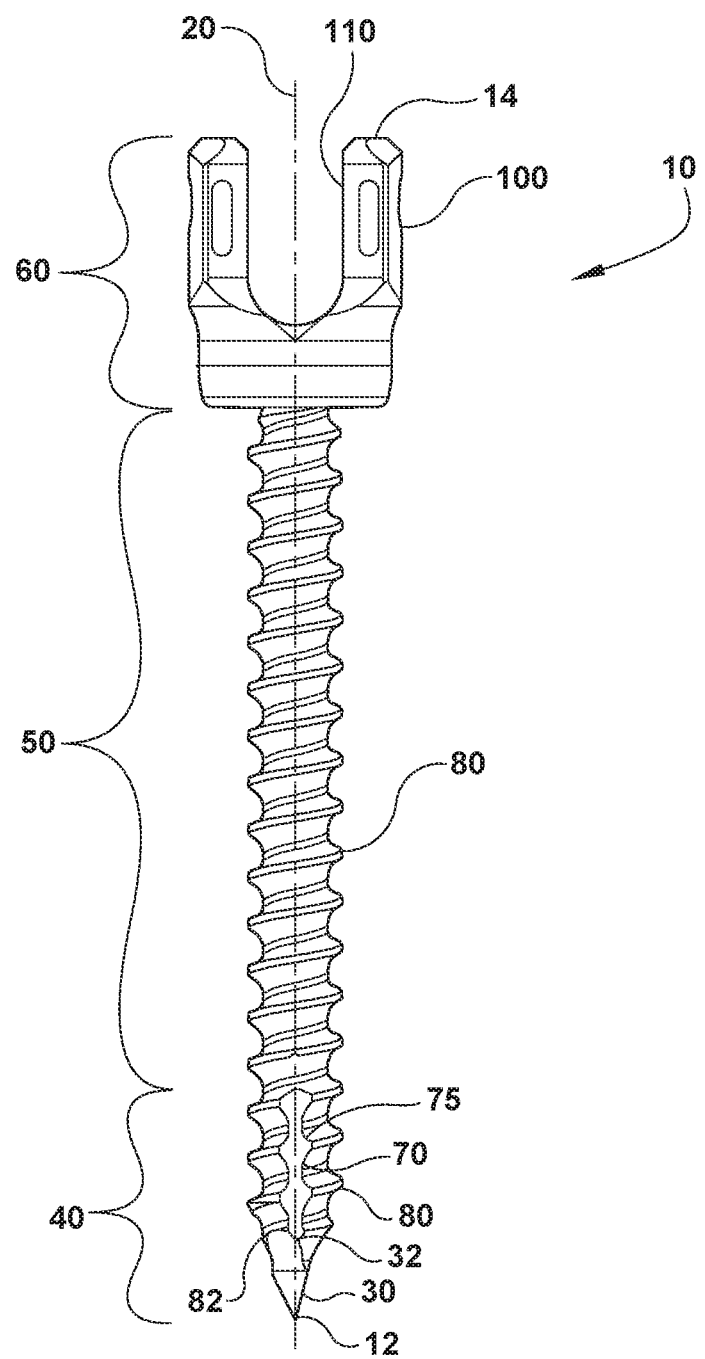
FIG. 1 is a side view of a bone screw according to one embodiment of the present disclosure.

For the purposes of promoting an understanding of the principles of the claimed technology and presenting its currently understood best mode of operation, reference will now be made to the embodiments illustrated in the drawings and specific language will be used to describe the same. It will nevertheless be understood that no limitation of the scope of the claimed technology is thereby intended, with such alterations and further modifications in the illustrated device and such further applications of the principles of the claimed technology as illustrated therein being contemplated as would normally occur to one skilled in the art to which the claimed technology relates.

A bone screw 10 according to one embodiment of the present disclosure is shown in FIG. 1. In the following description, the term "distal" will refer to the direction towards which a screw is designed to be advanced as the screw is engaged to bone and "proximal" will refer to the opposite direction. Bone screw 10 comprises several segments or portions which begin at a distal end 12 and extend along a longitudinal axis 20 to a proximal end 14. Located at distal end 12 of bone screw 10 is a tip portion 40 comprising an awl tip 30 and a helical, radially outward-extending thread 80. The awl tip is sized and configured so as to be capable of cutting, boring, or otherwise creating a pilot hole when placed against bone and torsional and/or downward force is applied to the screw, thereby eliminating the need for the separate steps for placing a pilot hole, drilling, probing, and tapping the hole during implantation. In some examples, the leading or distal edge 82 of the thread 80 begins at the proximal edge 32 of the awl tip 30. In other examples, the thread actually overlaps a portion of the awl tip. Typically, the leading edge of the thread is positioned such that as the awl tip excavates a hole in the bone, the leading edge engages the walls of the hole and draws the screw body into the bone. A variety of different thread styles and patterns may be used, including self-tapping threads, dual threads, and other suitable thread designs known in the industry. Optionally, tip portion 40 further includes one or more flutes 70 for conveying bone material away from the awl tip 30 and/or thread 80 during insertion of the screw into bone. In some examples, the flute 70 may also include a cutting edge 75 for engaging and removing bone material. The flute show in FIG. 1 is longitudinally disposed in the surface of the screw along axis 20, however other shapes, styles, and configurations of fluting may be used.

Figure 2:
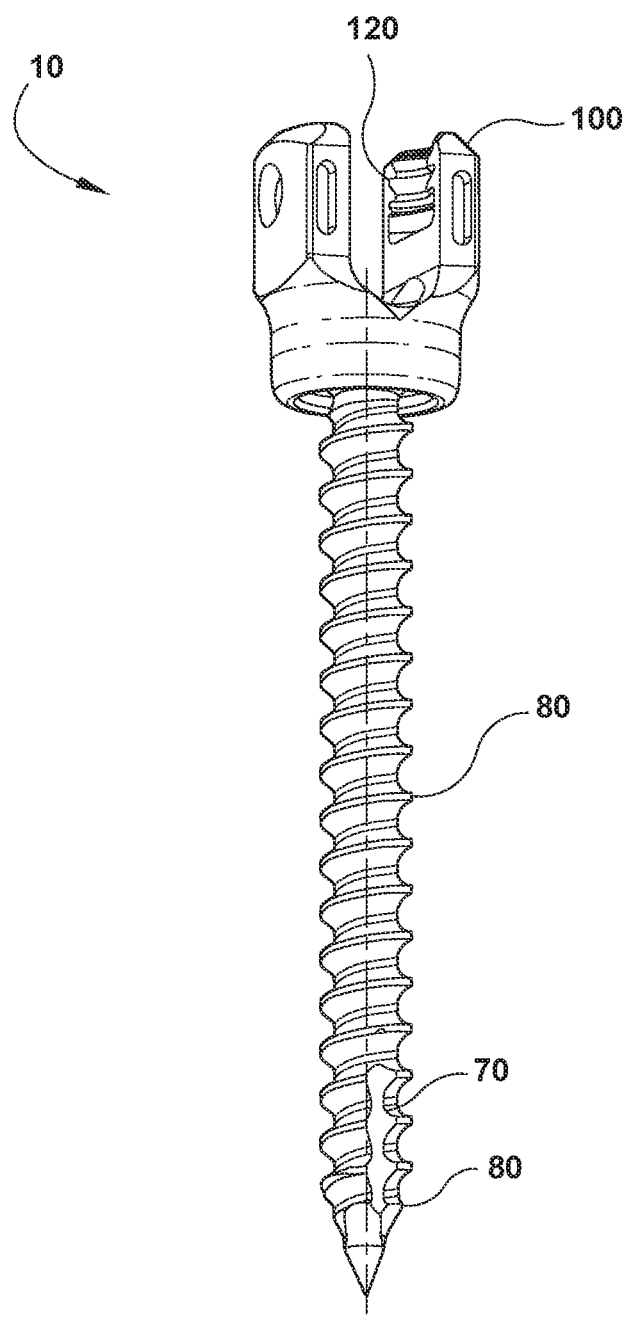
FIG. 2 is a perspective view of the bone screw shown in FIG. 1.

Adjacent to the proximal end of tip portion 40 is the distal end of a shank portion 50. The thread 80 from tip portion 40 continues through shank portion 50 to approximately the head portion 60 in this particular example. In other examples, a part of shank portion 50 may be unthreaded. Optionally, flute 70 which begins in tip portion 40 may continue or extend through a portion or all of shank portion 50. Adjacent to the proximal end of shank portion 50 and is the distal end of a head portion 60. In this particular embodiment, head portion 60 is shown comprising a U-shaped rod fixation element having a cradle 100 for receiving and securing rods (not shown) such as those commonly used in spinal procedures. Cradle 100 may further include a locking portion 120 (as shown in FIG. 2) for receiving and securing a locking member (not shown), such as a set screw, using a variety of locking means such as threads, bayonet style closure, and the like. Even though a fixed, U-shaped head assembly is shown in the present example, it is understood that other types and styles of head assemblies may also be used with the present disclosure such as a polyaxial head assembly, a hex head assembly, and any other mono-axial, mutli-axial, or fixed head design as known in the art.

Figure 3:
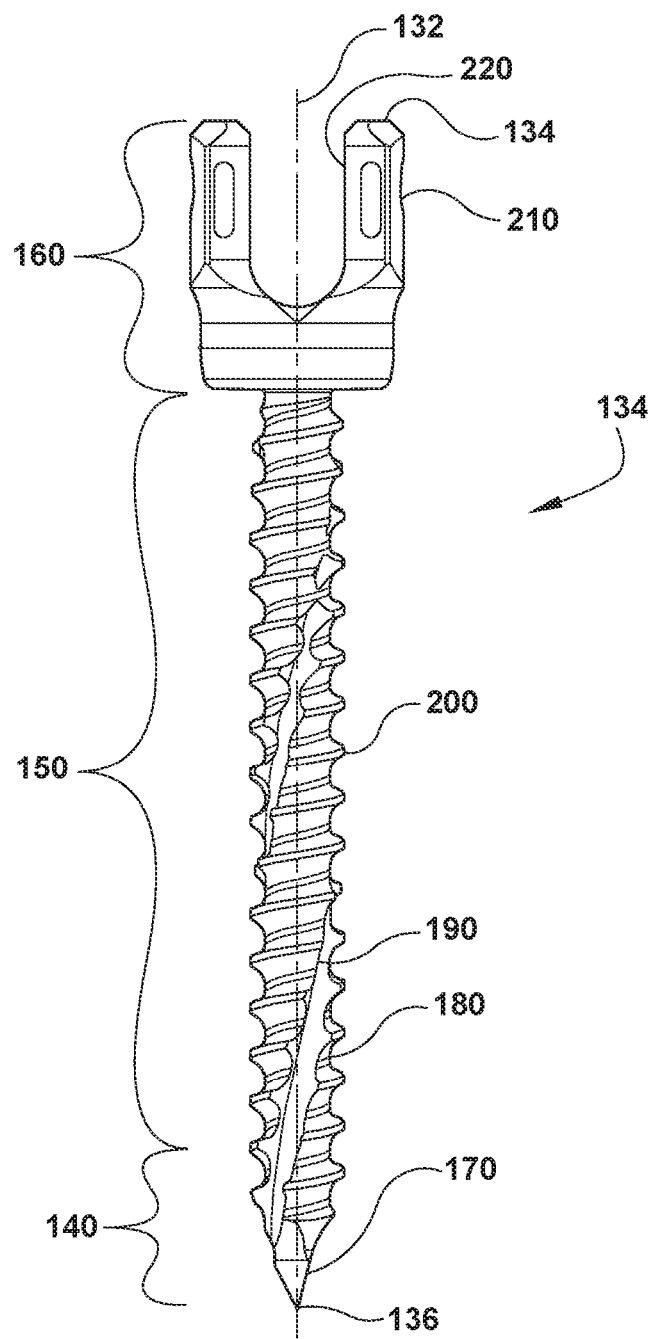
FIG. 3 is a side view of a bone screw according to another embodiment of the present disclosure.

A bone screw 130 according to another embodiment of the present disclosure is shown in FIGS. 3-6. Bone screw 130 comprises several segments or portions which begin at a distal end 136 and extend along a longitudinal axis 132 to a proximal end 134. Located at distal end 136 of bone screw 130 is a tip portion 140 comprising an awl tip 170 and a helical, radially outward-extending thread 200. A variety of different thread styles and patterns may be used, including self-tapping threads, dual threads, and other suitable thread designs known in the industry. Optionally, tip portion 140 further includes one or more flutes 180 for conveying bone material away from the awl tip 170 and/or thread 200 during insertion of the screw into bone. In some examples, the flute 180 may also include a cutting edge 190 for engaging and removing bone material. The flute show in FIG. 3 is an axially wound or spiral flute about the central body of screw 130 disposed along axis 132.

Figure 4:
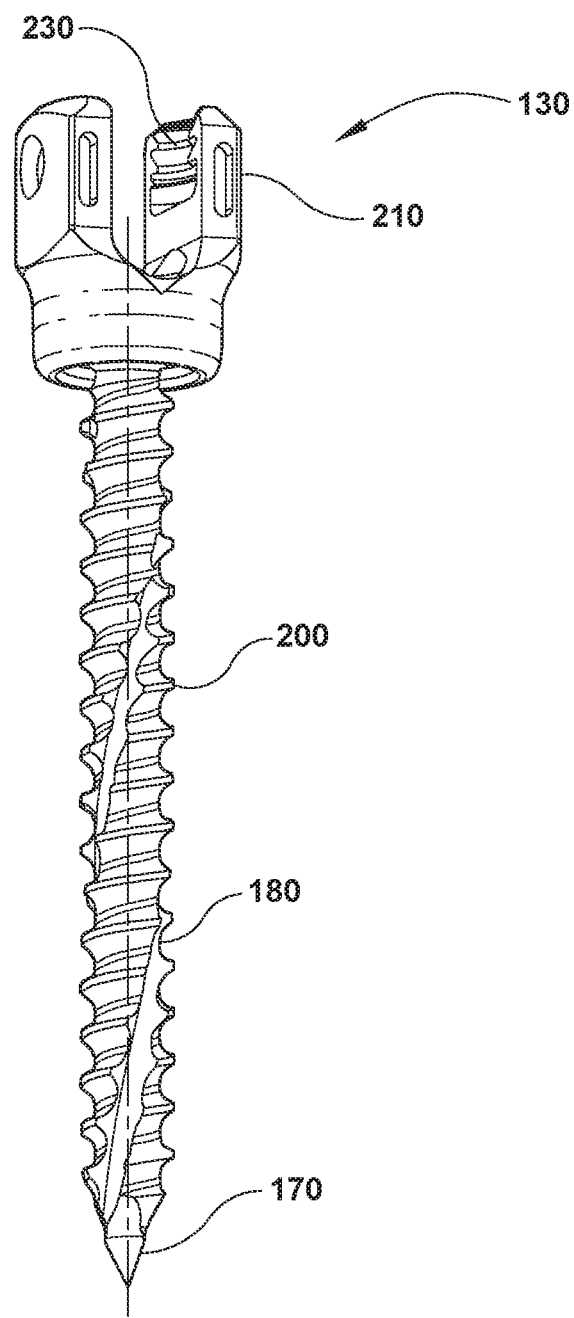
FIG. 4 is a perspective view of the bone screw shown in FIG. 3.
Figure 5:
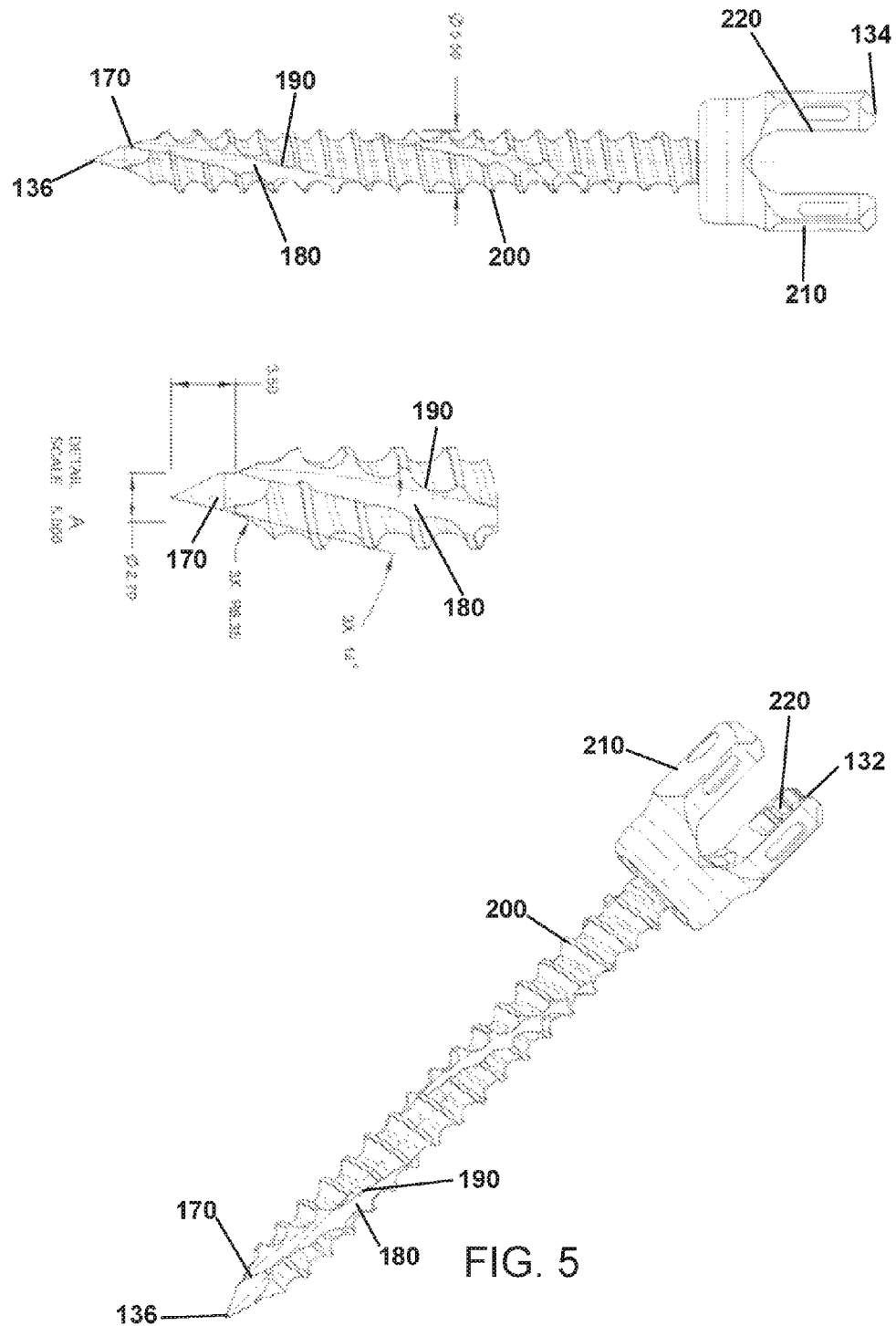
FIG. 5 is a side and perspective view of the bone screw shown in FIG. 3.
Figure 6:
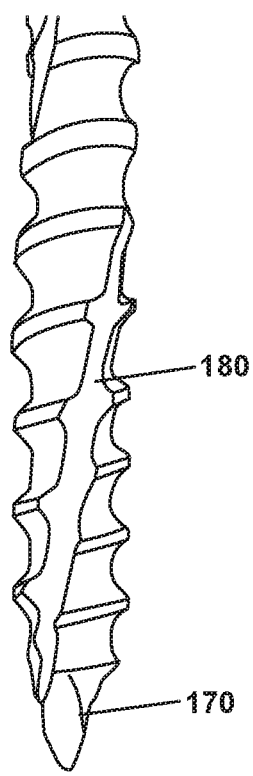
FIG. 6 is a side view of the bone screw shown in FIG. 3.

Adjacent to tip portion 140 is a shank portion 150. The thread 200 from tip portion 140 continues through shank portion 150 to approximately the head portion 160 in this particular example. In other examples, a part of shank portion 150 may be unthreaded. Flute 180 which begins in tip portion 140 continues through a portion of shank portion 150. Adjacent to shank portion 150 and continuing to the proximal end 134 of screw 130 is a head portion 210. In this particular embodiment, head portion 210 is shown comprising a U-shaped rod fixation element having a cradle 220 for receiving and securing rods (not shown) such as those commonly used in spinal procedures. Cradle 220 may further include a locking portion 230 (as shown in FIG. 4) for receiving and securing a locking member (not shown) using a variety of locking means such as threads, bayonet style closure, and the like. Even though only a U-shaped head assembly is shown in the present example, it is understood that other types and styles of head assemblies may also be used with the present disclosure such as a polyaxial head assembly, hex head assembly, and the like.

Figure 7:
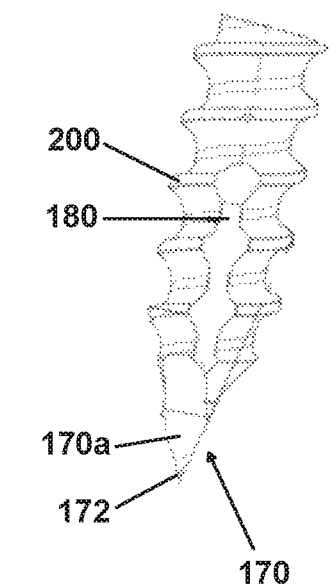
FIG. 7 is a partial view of tips in accordance with the present disclosure.
Figure 7:
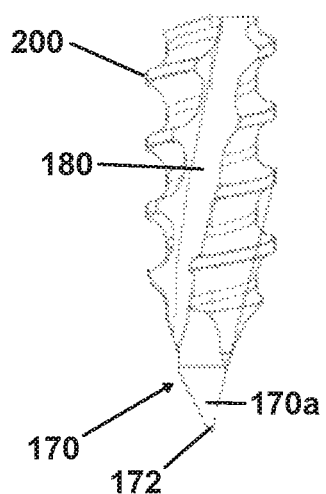
Figure 7A:
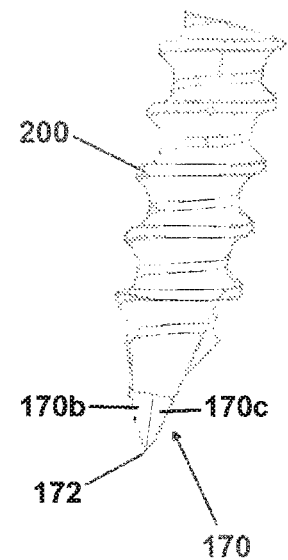
FIG. 7A is a partial view of the tips shown in FIG. 7, with the tips shown in FIG. 7 rotated 180 degrees about longitudinal axes defined by the bone screws.
Figure 7A:
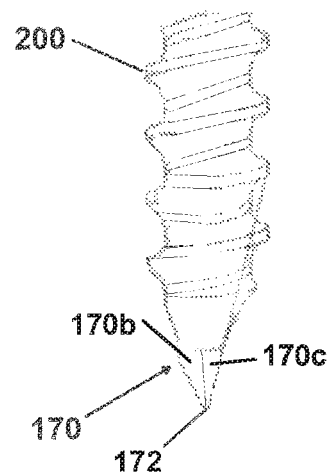

In some embodiments, awl tip 170 has a pyramidal configuration, as shown in FIGS. 7 and 7A. In some embodiments, awl tip 170 comprises a plurality of planar surfaces, such as, for example, planar surfaces 170a, 170b, 170c. Planar surfaces 170a, 170b, 170c each extend at an angle relative to one another, such as, for example, an acute angle. That is, planar surface 170b extends at an acute angle relative to planar surface 170a and planar surface 170c and planar surface 170c extends at an acute angle relative to planar surface 170a and planar surface 170c. In some embodiments, planar surfaces 170a, 170b, 170c intersect at a common point, such as, for example, a distalmost tip 172. That is, planar surfaces 170a, 170b, 170c converge at tip 172. In some embodiments, tip 172 is a sharp tip, as shown in FIGS. 7 and 7A. In some embodiments, flute 180 extends parallel to a longitudinal axis defined by shank portion 150. In some embodiments, flute 180 extends at an acute angle relative to a longitudinal axis defined by shank portion 150.

Screw Implantation

Placement of a bone screw according to the present disclosure does not require the multi-step procedure commonly used in the industry and previously described.

One method of implanting a bone screw according to the present disclosure comprises placing the awl tip against the vertebra at the desired entry point, typically at the surface of a pedicle. Torsional force is applied to the bone screw using a driving tool engaged with the head of the screw. Typically the driving tool will be an image guided and navigated tool, such as a screw driver, to allow the surgeon to confirm the correct trajectory of the screw through the bone. In other examples, guidance techniques such as anatomic landmarks or fluoroscopy may also be used to insure proper screw placement. As torsional force is applied to the screw, the awl tip engages and begins to carve a hole into the bone. Once the awl has carved a hole of sufficient depth the threads will engage the bone. Typically, the thread (or threads if a multi-thread design is used) of the screw begin immediately adjacent to the awl tip so as to reduce the depth to which the screw must be driven before the screw engages the bone.

Once the screw threads have engaged the bone, the threads act to draw the screw down into the vertebra while the awl tip continues to carve out bone at the tip of the screw. If the screw also includes one or more flutes, the flutes act to channel bone material away from the tip and thread so as to increase performance of the screw. As the threads act to pull the screw down into the bone less force will need to be applied by the surgeon. Proper placement of the screw can be confirmed using imaging. Additional confirmation may be provided using neuromonitoring to insure there is no nerve irritation. Once the desired implantation depth is reached, additional elements such as rods, plates, and the like, may be secured to the screw using appropriate means.

Figure 8:
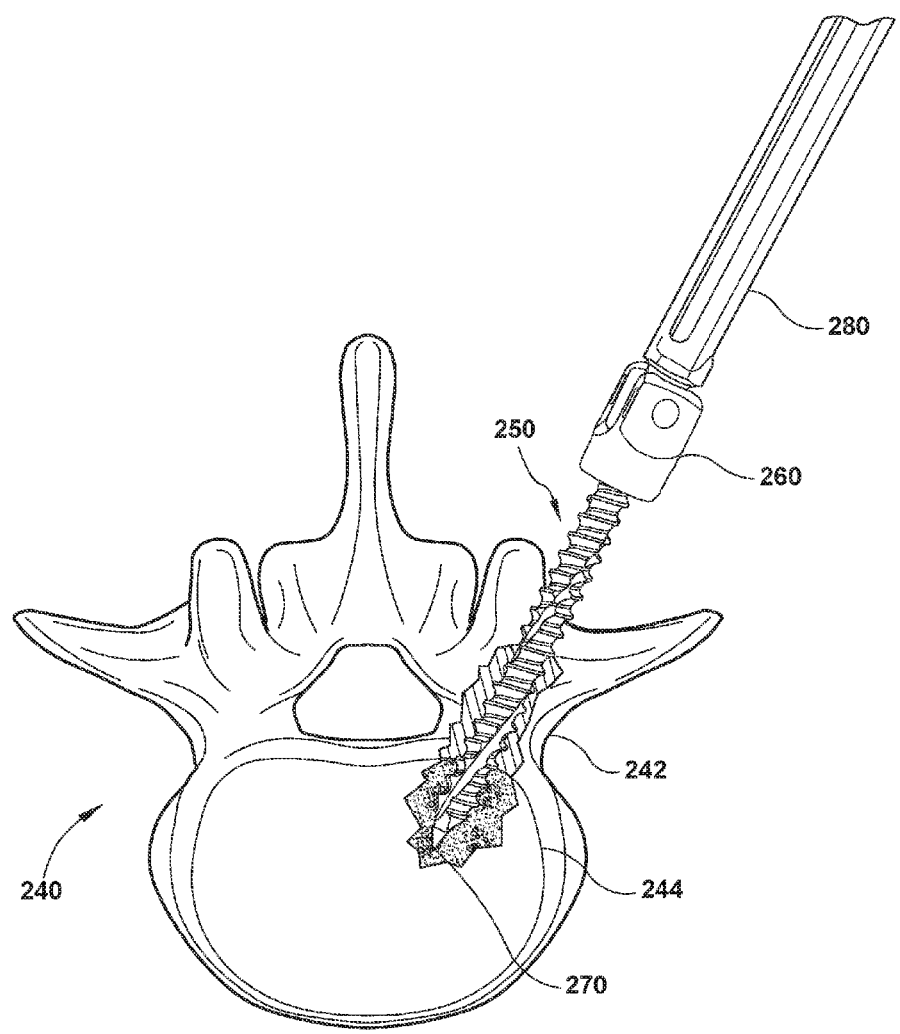
FIG. 8 is a side, cross sectional view of a bone screw being inserted into the pedicle of a spine according to one embodiment of the present disclosure.
Figure 3:
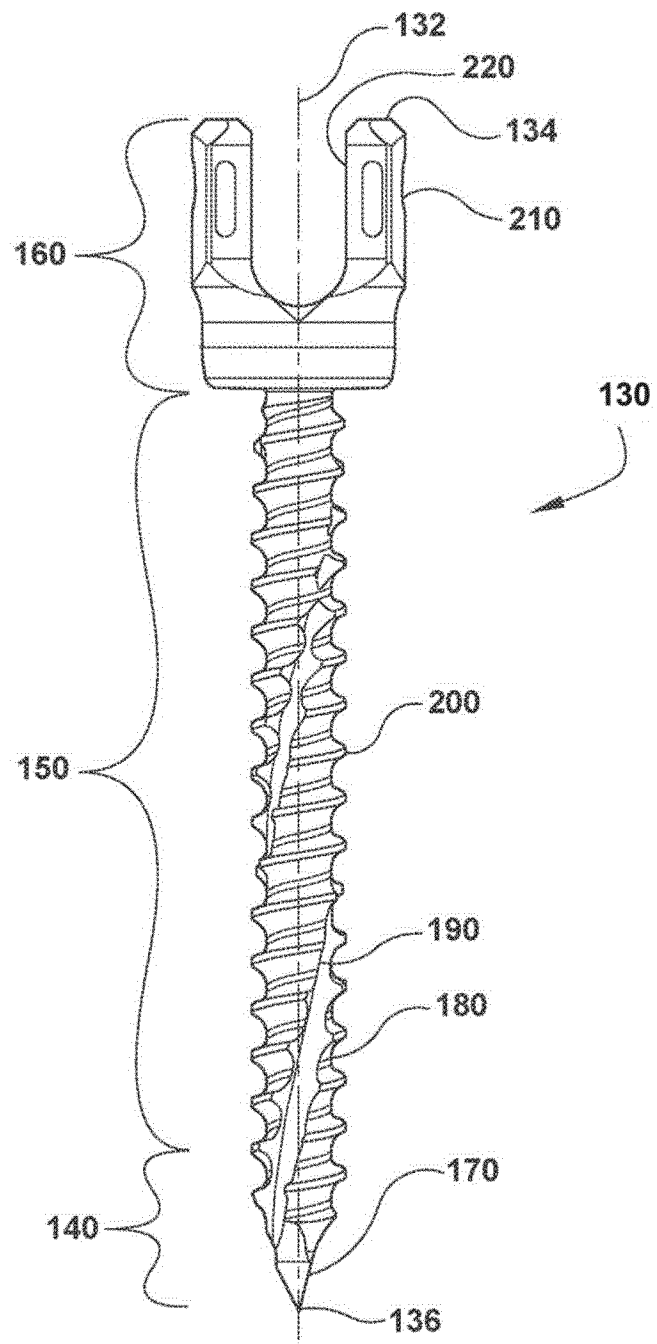

FIG. 8 shows the implantation of a bone screw in a vertebra according to one embodiment of the present disclosure. In this particular example, a bone screw 250 such as those previously described is implanted in vertebra 240. An awl tip 270 allows the screw 250 to be driven into the bone of the vertebra, specifically through the body of a pedicle 242 and into the vertebral body 244. Bone screw 250 includes a head portion 260 which is configured and adapted to engage a suitable driving tool 280 which allows for implantation of the screw. Optionally, driving tool 280 is an image guided and navigated tool, such as a screw driver, to allow for confirmation of the trajectory of the screw through the pedicle. Image guided navigation allows a surgeon to confirm proper placement of the screw in the bone. Additionally, the harder cortical bone walls of the pedicle will encourage the screw to follow a trajectory through the softer, cancellous bone found in the center of the pedicle. Imaging may be used to confirm proper screw placement. Additionally, neuromonitoring may be used to confirm there is no nerve root irritation while the screw is being placed. Once placed, additional elements such as rods, plates, and the like, may be secured to the screw using appropriate means.

Reducing the number of steps in the implantation procedure using the devices and methods previously described decreases the time required for a procedure. Less time in the operating room means less blood loss, decreased risk of infection and the patient spends less time sedated, thereby reducing the possibility of anesthesia-related complications. Elimination of preparatory steps required for the placement of current bone screw designs also decreases the opportunities for mistakes during implantation, especially during long procedures involving the implantation of multiple screws where surgeon fatigue can become a factor.

While the claimed technology has been illustrated and described in detail in the drawings and foregoing description, the same is to be considered as illustrative and not restrictive in character. It is understood that the embodiments have been shown and described in the foregoing specification in satisfaction of the best mode and enablement requirements. It is understood that one of ordinary skill in the art could readily make a nigh-infinite number of insubstantial changes and modifications to the above-described embodiments and that it would be impractical to attempt to describe all such embodiment variations in the present specification. Accordingly, it is understood that all changes and modifications that come within the spirit of the claimed technology are desired to be protected.

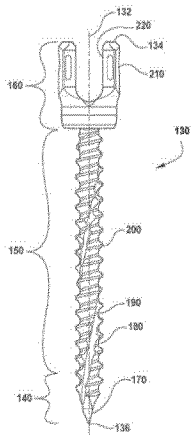

What is claimed is:

1. A bone screw, comprising:
a tip portion comprising an awl tip and a tapered portion proximate to said awl tip, said awl tip comprising a plurality of flat surfaces, said awl tip having a pyramidal configuration capable of creating a hole in bone;
a shank portion proximate to said tapered portion;
a head portion proximate to said shank portion, said head portion being rotatable relative to said shank portion; and
at least one helical thread which begins at said tapered portion and continues through said shank portion, said tapered portion being continuously tapered from at least a distal end of said at least one helical thread to said plurality of flat surfaces, said shank portion comprising a spiral flute that extends through said at least one helical thread and into said tapered portion.

2. The bone screw of claim 1, wherein said plurality of flat surfaces comprises three flat surfaces.

3. The bone screw of claim 1, wherein said plurality of flat surfaces comprises three flat surfaces, said flat surfaces intersecting at a common point.

4. The bone screw of claim 1, wherein said plurality of flat surfaces comprises three flat surfaces that converge at a distalmost tip of the tip portion.

5. The bone screw of claim 1, wherein said flute extends through all of said shank portion.

6. The bone screw of claim 1, wherein said flute extends continuously from said shank portion to said tapered portion.

7. The bone screw of claim 1, wherein said flute further comprises a cutting edge.

8. A pedicle screw, comprising:
a tip portion located at a distal end of said pedicle screw, said tip portion comprising an awl tip and a tapered portion proximate to said awl tip, said awl tip comprising a plurality of flat surfaces, said awl tip having a pyramidal configuration capable of starting a hole in bone;
a head portion located at a proximal end of said pedicle screw;
a shank portion disposed between said tapered portion and said head portion, said head portion being rotatable relative to said shank portion; and
at least one thread beginning at said tapered portion and continuing in said shank portion, said at least one thread overlapping a portion of said awl tip, said tapered portion being continuously tapered from at least a distal end of said at least one thread to said plurality of flat surfaces, said shank portion comprising a spiral flute that extends through said at least one thread and into said tapered portion.

9. The bone screw of claim 8, wherein said plurality of flat surfaces comprises three flat surfaces.

10. The bone screw of claim 8, wherein said plurality of flat surfaces comprises three flat surfaces, said flat surfaces intersecting at a common point.

11. The bone screw of claim 8, wherein said plurality of flat surfaces comprises three flat surfaces that converge at a distalmost tip of the tip portion.

12. The pedicle screw of claim 8, wherein said flute extends through all of said shank portion.

13. The pedicle screw of claim 8, wherein said flute extends into said shank portion.

14. The pedicle screw of claim 8, wherein said flute extends continuously from said shank portion to said tapered portion.

15. The pedicle screw of claim 8, wherein said flute further comprises a cutting edge.

16. A bone screw, comprising:
a tip portion, comprising an awl tip, a tapered portion proximate to said awl tip and at least one thread, said awl tip comprising a plurality of flat surfaces;
a shank portion, located proximate to said tapered portion and comprising part of the at least one thread of the tip portion, said shank portion comprising a spiral flute that extends through said at least one thread and into said tapered portion; and
a head portion proximate to said shank portion and adapted to receive a driving tool, said head portion being rotatable relative to said shank portion;
wherein said awl tip has a pyramidal configuration capable of creating a hole in bone when torsional force is applied to the screw;
wherein said tapered portion is continuously tapered from a distal end of said at least one thread to said plurality of flat surfaces, said at least one thread being configured to engage walls of the hole created by said awl tip and draw the screw into bone.

17. The bone screw of claim 16, wherein said plurality of flat surfaces comprises three flat surfaces.

18. The bone screw of claim 16, wherein said plurality of flat surfaces comprises three flat surfaces, said flat surfaces intersecting at a common point.

19. The bone screw of claim 16, wherein said plurality of flat surfaces comprises three flat surfaces that converge at a distalmost tip of the tip portion.

20. The bone screw of claim 16, wherein said at least one thread is spaced apart from said flat surfaces.

\* \* \* \* \*

UNITED STATES PATENT AND TRADEMARK OFFICE
CERTIFICATE OF CORRECTION

PATENT NO. : 9,949,776 B2  
APPLICATION NO. : 15/159426  
DATED : April 24, 2018  
INVENTOR(S) : Mobasser et al.

Page 1 of 1

It is certified that error appears in the above-identified patent and that said Letters Patent is hereby corrected as shown below:

In Column 1, Line 8, delete "14/011,052," and insert -- 14/011,052 filed on Aug. 27, 2013, now abandoned, --, therefor.

In Column 1, Line 11, delete "2011," and insert -- 2011, now abandoned, --, therefor.

In Column 1, Line 11, delete "Patent No." and insert -- Patent Application No. --, therefor.

In Column 1, Line 13, delete "reference," and insert -- reference --, therefor.

In Column 3, Line 6, delete "show" and insert -- shown --, therefor.

In Column 3, Line 47, delete "show" and insert -- shown --, therefor.

In Column 6, Line 23, in Claim 9, delete "bone screw" and insert -- pedicle screw --, therefor.

In Column 6, Line 25, in Claim 10, delete "bone screw" and insert -- pedicle screw --, therefor.

In Column 6, Line 28, in Claim 11, delete "bone screw" and insert -- pedicle screw --, therefor.

Signed and Sealed this  
Twenty-seventh Day of November, 2018

Andrei Iancu  
*Director of the United States Patent and Trademark Office*

UNITED STATES PATENT AND TRADEMARK OFFICE
CERTIFICATE OF CORRECTION

| | |
|---|---|
| PATENT NO. | : 9,949,776 B2 |
| APPLICATION NO. | : 15/159426 |
| DATED | : April 24, 2018 |
| INVENTOR(S) | : Mobasser et al. |

It is certified that error appears in the above-identified patent and that said Letters Patent is hereby corrected as shown below:

Delete the title page and substitute therefore with the attached title page consisting of the corrected illustrative figure.

Please replace FIG. 3 with FIG. 3 as shown on the attached page.

Signed and Sealed this
Fifth Day of May, 2020

Andrei Iancu
*Director of the United States Patent and Trademark Office*

(12) United States Patent
Mobasser et al.

(10) Patent No.: US 9,949,776 B2
(45) Date of Patent: Apr. 24, 2018

(54) AWL-TIPPED PEDICLE SCREW AND METHOD OF IMPLANTING SAME

(71) Applicant: WARSAW ORTHOPEDIC, INC., Warsaw, IN (US)

(72) Inventors: Jean-Pierre Mobasser, Indianapolis, IN (US); Y. Raja Rampersaud, Toronto (CA)

(73) Assignee: Warsaw Orhtopedic, Inc., Warsaw, IN (US)

(*) Notice: Subject to any disclaimer, the term of this patent is extended or adjusted under 35 U.S.C. 154(b) by 0 days.

(21) Appl. No.: 15/159,426

(22) Filed: May 19, 2016

(65) Prior Publication Data

US 2016/0256209 A1    Sep. 8, 2016

Related U.S. Application Data

(63) Continuation of application No. 14/011,052, filed on Aug. 27, 2013, now abandoned, which is a continuation-in-part of application No. 13/117,669, filed on May 27, 2011, now abandoned.

(60) Provisional application No. 61/396,564, filed on May 28, 2010.

(51) Int. Cl.
*A61B 17/86* (2006.01)
*A61B 17/70* (2006.01)

(52) U.S. Cl.
CPC ........ *A61B 17/8635* (2013.01); *A61B 17/863* (2013.01); *A61B 17/7037* (2013.01)

(58) Field of Classification Search
CPC ... A61B 17/86; A61B 17/8605; A61B 17/861; A61B 17/8615; A61B 17/862; A61B 17/8625; A61B 17/863; A61B 17/8635; A61B 17/866; F16B 25/0015
USPC ....... 606/300–321, 246–279; 411/386, 387.1
See application file for complete search history.

(56) References Cited

U.S. PATENT DOCUMENTS

| 373,074 | A | * | 11/1887 | Jones | F16B 25/00 411/386 |
| 2,871,752 | A | * | 2/1959 | Stern | F16B 25/0031 411/387.1 |
| 4,068,554 | A | * | 1/1978 | Hirabayashi | F16B 25/0021 411/386 |
| 4,311,423 | A | * | 1/1982 | Hirabayashi | F16B 25/0021 411/387.4 |
| 4,572,720 | A | * | 2/1986 | Rockenfeller | F16B 15/06 411/311 |

(Continued)

OTHER PUBLICATIONS

Yan Chen, Hong-In Shin, Hee-Moon Kyung Biomechanical and histological comparison of self-drilling and self-tapping orthodontic microimplants in dogs American Journal of Orthodontics and Dentofacial Orthopedics, vol. 133, Issue 1, Jan. 2008, pp. 44-50.

(Continued)

*Primary Examiner* — Eric S Gibson

(57) ABSTRACT

A bone screw and method of inserting the same is disclosed. In one example, the bone screw includes an awl tip for creating a pilot hole in the pedicle of a vertebra without having to predrill a starter hole. One or more threads located adjacent to the awl tip engage the wall of the pilot hole and draw the screw into the bone, thereby eliminating the need to drill and tap a hole in the bone prior to implantation of the screw.

20 Claims, 9 Drawing Sheets